United States Patent [19]

Diem et al.

[11] 4,001,337

[45] Jan. 4, 1977

[54] STABILIZED AQUEOUS FORMALDEHYDE SOLUTIONS AND PROCESS FOR THEIR MANUFACTURE

[75] Inventors: Hans Diem; Herbert Libowitzky; Guenther Matthias; Christian Dudeck; Gunter Lehmann, all of Ludwigshafen, Germany

[73] Assignee: BASF Aktiengesellschaft, Ludwigshafen (Rhine), Germany

[22] Filed: Nov. 13, 1974

[21] Appl. No.: 523,443

[30] Foreign Application Priority Data

Nov. 26, 1973 Germany .......................... 2358856

[52] U.S. Cl. ............................................. 260/606
[51] Int. Cl.[2] ...................................... C07C 47/04
[58] Field of Search ................................... 260/606

[56] References Cited

UNITED STATES PATENTS 3,651,056   3/1972   Muruyama et al. ............... 260/606

FOREIGN PATENTS OR APPLICATIONS 1,205,071   11/1965   Germany ......................... 260/606

*Primary Examiner*—James O. Thomas, Jr.
*Assistant Examiner*—W. B. Lone
*Attorney, Agent, or Firm*—Johnston, Keil, Thompson & Shurtleff

[57] ABSTRACT

Stabilized, aqueous formaldehyde solutions and a process for their manufacture by addition of isophthalobisguanamine and/or terephthalo-bis-guanamine. The formaldehyde solution of the invention is used as a disinfectant, tanning agent or reducing agent, and as a starting material for the manufacture of synthetic resins, adhesives and plastics.

6 Claims, No Drawings

STABILIZED AQUEOUS FORMALDEHYDE SOLUTIONS AND PROCESS FOR THEIR MANUFACTURE

This application discloses and claims subject matter described in German Patent Application No. P 23 58 856.9, filed Nov. 26, 1973, which is incorporated herein by reference.

The invention is concerned with stabilized, aqueous formaldehyde solutions and a process for their manufacture by addition of isophthalo-bis-guanamine and/or terephthalo-bis-guanamine.

It is known that polymers separate out from aqueous formaldehyde solutions on standing at low temperatures (J. F. Walker, Formaldehyde, New York, 3rd edition 1964, pages 94 and 120; U.S. Pat. No. 3,637,861, column 1, lines 27–45; U.S. Pat. No. 3,532,756, column 1, lines 43–60; German Printed Application No. 1,443,566, column 1, lines 33 et seq.). This separation of polymer increases with increasing formaldehyde concentration at concentrations above 30% by weight of formaldehyde, with the period of storage and with decreasing temperature. It is undesirable because the solid polymer which has separated out also settles out, blocks the valves and pumps and leads to differences in the concentration between the upper and lower layers of the stored solutions (Walker, loc.cit., page 94). The presence of undissolved constituents in the formaldehyde solution, or the constant formation of a precipitate, also interferes in chemical reactions, for example in the manufacture of glue. An added factor to consider is that solutions should be as concentrated as possible in order to save transport costs and simplify the operation.

It is possible to differentiate between the following methods of stabilization according to the mode of action (Walker, loc.cit., page 94): the best-known additive is methanol, which reacts with the dissolved formaldehyde. This stabilizer has to be present in amounts of at least from 10 to 15% by weight, that is to say in relatively high concentration. Hence, methanol is an uneconomical stabilizer and must, moreover, be recovered by distillation when using the stabilized formaldehyde. Manipulations of sizable amounts of this product create problems in industrial operation, because of the toxicity of the product. Methanol frequently increases the difficulty of processing the formaldehyde; for example, it has an adverse influence on condensation reactions such as the manufacture of glue from formaldehyde and urea, and the operation of concentrating the glue requires larger kettles and larger condensers. Furthermore, the addition of methanol as a stabilizer dilutes the formaldehyde solution. In order finally to arrive at the same concentration as with a non-stabilized solution, it is necessary to start from a particularly concentrated solution, which also entails additional costs.

Stabilizers have also been disclosed which prevent the condensation reactions which lead to sparingly soluble polymers, or prevent the crystallization or precipitation of polymers already present. These categories appear to include the materials which increase the viscosity of the solution, for example agar-agar, methylcellulose, gelatine, pectins and other colloids (German Printed Application No. 1,293,734, column 1, lines 26 et seq; German Printed Application No. 1,443,566). However, formaldehyde solutions stabilized in this way turn to pastes at low temperatures and have to be redissolved carefully by warming (German Printed Application No. 1,205,071, column 1, lines 44–52). Many additives which decrease the polymerization, or the crystallization or precipitation of polymers, have already been disclosed. These include the following: vinyl polymers, vinyl copolymers, acid anhydrides, UV-treated substances such as esters and acids, and amines; urea, thiourea, urea derivatives such as diethylthiourea, methylurea and dimethylolurea, and nitroguanidine; phenol, phenol derivatives, barbiturates, polyalcohols and polyhydroxyacetals; alkanols such as propanol, isopropanol and ethanol; acetoxime, glycine, glycol, glycerol and urates. To decrease crystallization or precipitation of polymers, substantial amounts of these materials must be used; hence this method is uneconomical and/or the formaldehyde solution thus stabilized can only be used for certain syntheses, for example, in the case of adding urea, for the reaction of formaldehyde with urea (to manufacture adhesives). Esters of polyalcohols, for example esters of sorbitol with fatty acids, acid amides and thioacid amides, for example chloroacetamide and formamide, and polyvinyl alcohol, when used as stabilizers, can be used in smaller amounts, but in that case have an unsatisfactory stabilizing action.

Hydroxyethylcellulose is described in U.S. Pat. No. 3,532,756. Alkylated carbohydrates, such as hydroxyethylcellulose and methylcellulose, produce heavy foaming (U.S. Pat. No. 3,637,861, column 2, lines 11–23), which interferes with any subsequent processing and makes it necessary to add an antifoaming agent. Thus, in the process described in U.S. Pat. No. 3,637,861, the alkylated celluloses are only employed in conjunction with silanes. To achieve stabilization over a prolonged period, substantial amounts of the additives are required (Table II of U.S. Pat. No. 3,637,861; German Printed Application No. 1,768,915, column 2, lines 24–26). Furthermore, silanes containing chlorine are used in particular, whilst for both chemical reasons and health reasons it is necessary that the formaldehyde solutions, if they are to be processed further, should be kept free from chlorine.

Nitrogen-containing heterocyclic compounds are a further group of stabilizers. Melamine, which is one of those used frequently (German Patent No. 1,251,730) has the disadvantage that high concentrations of stabilizer are necessary and nevertheless the stabilizing action is inadequate. Because of the large amounts of melamine required, the corresponding formaldehyde solutions can only be used for certain reactions, for example for the manufacture of melamine-formaldehyde resins. If the formaldehyde solutions stabilized in this way are alkaline, substantial amounts of alkali metal formate form and the buffer action of this compound handicaps the subsequent conversion of such solutions to aminoplast condensates and reduces the water resistance of the cured resins. Furthermore, methylolmelamine compounds and paraformaldehyde separate out from alkaline melamine-formaldehyde solutions on standing at room temperature for several hours or at most after a few days. As a result, the solutions become turbid and can, in extreme cases, even set solid. It is therefore necessary to use such alkaline absorption solutions very rapidly.

If attempts are made to circumvent these disadvantages by carrying out the absorption at an acid pH, the cited patent specifications state that clear and stable melamine-formaldehyde solutions can only be obtained if these also contain methanol. However, in that case the methanol in the main reacts with the hydroxyl groups of the melamine-formaldehyde condensation products present in solution, to form ethers. This blocks hydroxyl groups and lowers the rate of condensation of these precondensates, making these solutions difficult to use. Furthermore, the methanol constituent is lost during the manufacture of formaldehyde.

Substituted triazines, for example benzoguanamine

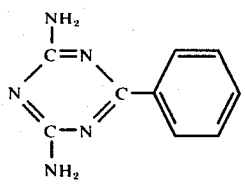

acetoguanamine and other guanamines substituted in the 6-position have also been disclosed as stabilizers. These triazines, claimed in Belgian Patent No. 664,428 and German Printed Applications Nos. 1,205,071 and 1,205,073 however produce copious foaming, particularly if they contain long-chain aliphatic radicals (German Printed Application No. 1,768,915, column 3, lines 10–35). For this reason, mixtures of major amounts of melamine and the conventional amounts of substituted triazines are used in the process described in German Printed Application No. 1,768,915. Analogously to the solutions containing pure melamine, such solutions, because of the high melamine content, suffer from the disadvantage of containing a substantial proportion of foreign matter. Since the above guanamines are difficult to obtain or expensive to manufacture, such additives are economically unsatisfactory even though the stabilizing action is better.

German Printed Application No. 1,205,071 also describes o-phthaloguanamine

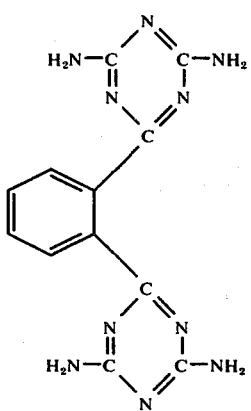

Examples 14 shows the stabilizing action of this substance, which is insignificant, whilst the concentration of stabilizer, namely 2%, is unusually high. It is also known that resins, manufactured from formaldehyde stabilized with phenyl-substituted triazines, discolor on exposure to ultraviolet, including the ultraviolet in daylight (German Printed Application No. 1,205,073, column 1, lines 17–32).

A good stabilizer must have a high stabilizing action even at low concentration and must not alter the physical properties of the aqueous formaldehyde solutions in which it is used; it should also be capable of stabilizing solutions of high concentration, for example of more than 45 per cent by weight. In their overall properties, all the above stabilizers are unsatisfactory in this context.

Some stabilizing action is also achieved by raising the temperature and diluting the formaldehyde solution but both measures are frequently undesirable, uneconomical or not feasible under the particular conditions.

It is an object of the present invention to provide a new process for simpler and more economical manufacture of stabilized aqueous formaldehyde solutions, which uses small amounts of stabilizers and achieves a high stabilizing action.

Another object is the new aqueous formaldehyde solutions containing bis-guanamines.

We have found that an advantageous method of stabilizing aqueous formaldehyde solutions is to use bis-guanamines of the formula

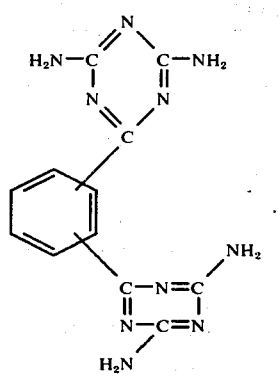

I wherein the two substituents on the phenylene ring are in the m-position or p-position to one another, as stabilizers.

We have also found that aqueous formaldehyde solutions containing bis-guanamine I, wherein the two substituents on the phenylene ring are in the m-position or p-position to one another, display advantages.

Compared to the state of the art, the process of the invention gives stabilized, aqueous formaldehyde solutions more simply and more economically, uses small amounts of stabilizers and achieves a high stabilizing action. Compared to all conventional stabilizers which do not contain the guanamino group, isopthalo-bis-guanamine and terephthalo-bis-guanamine need only be used in small amounts, have a greater stabilizing action, do not require the addition of anti-foaming agents and are more economical; the formaldehyde solutions thus stabilized can be used for all syntheses and all applications. The new method of stabilization is also more suitable from the point of view of health care and protection of the environment, since the stabilizers according to the invention contain no markedly toxic groups or atoms, for example chlorine atoms.

Surprisingly, and unlike the guanamine stabilizers which have been mentioned, for example those with long-chain alkyl radicals, the stabilizers according to the invention do not increase the foaming of the solutions.

It is also surprising that they produce highly stable solutions even when used in small amounts, in contrast to o-phthaloguanamine which hardly has a stabilizing action, and that the resins manufactured from formaldehyde solutions stabilized according to the invention display no significant discoloration on exposure to ultraviolet, in contrast to the situation when phenyl-substituted guanamines, for example benzoguanamine, are used.

The formaldehyde can be manufactured by any desired method, for example by the oxidative dehydrogenation of methanol with air in the presence of a silver catalyst or in the presence of metal oxides, for example molybdenum oxide, iron oxide, chromium oxide, cobalt oxide, tungsten oxide, nickel oxide, vanadium oxide and/or bismuth oxide, or by oxidation of methane or higher hydrocarbons, for example alkanes and alkenes of 2 to 4 carbon atoms, in the presence of metal oxides, for example those mentioned above. Other methods of manufacture, such as the partial catalytic reduction of carbon monoxide or carbon dioxide, the pyrogenic production from formic acid or formates, or the saponification of methylene chloride or methylal can also be used. Details of the methods of manufacture are to be found in Ullmanns Encyklopadie der technischen Chemie, volume 7, pages 659 et seq. The aqueous solution can be manufactured in various ways; suitable solutions to use are the aqueous absorption solutions produced by manufacturing the formaldehyde in the gas phase and then passing the reaction mixture into water. The absorption solutions can subsequently be concentrated if desired, for example by distillation, preferably fractional distillation, if appropriate whilst passing steam or an inert gas into the mixture, and advantageously followed by fractional condensation.

The solution can, for example, be manufactured by conventional methods comprising passing a gas mixture of methanol vapor, air, and optionally an inert gas and steam through a silver catalyst at temperatures from about 550° to 780° C, especially from 640° to 750° C. The reaction gases leaving the catalyst zone should preferably be chilled, for example to temperatures of from 50° to 160° C, within a short time, for example in less than 0.2 second. The cooled gas mixture is then led to an absorber tower in which the formaldehyde is washed out of the gas mixture by means of water, advantageously in counter-current.

The stabilizers used are terephthalo-bis-guanamine

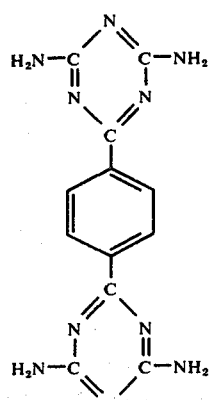

and preferably isophthalo-bis-guanamine

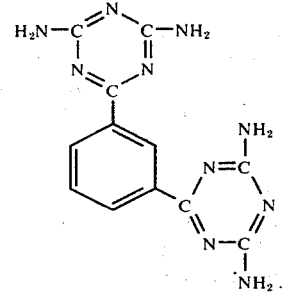

These guanamines can be manufactured by reaction of isophthalonitrile or terephthalonitrile with dicyandiamide, for example by the method described in German Printed Application No. 1,019,310. As a rule, the stabilizer is used in amounts from 0.001 to 0.5% by weight, preferably from 0.005 to 0.25% by weight, and especially from 0.01 to 0.08% by weight, based on the formaldehyde solution.

The concentrations of the solutions to be stabilized are in general up to 65% by weight, suitably from 28 to 65% by weight, advantageously from 30 to 54% by weight, and especially from 44 to 54% by weight of formaldehyde (taken to be 100% strength). The solutions can contain other materials, especially materials originating from the manufacture of the formaldehyde. Thus, the following materials may be present in the solutions: alkanols, especially methanol, for example from 1 to 20% by weight, and preferably from 1 to 3% by weight, of methanol, based on formaldehyde (taken to be 100% strength); formic acid, for example from 0.001 to 0.2% by weight; impurities and by-products, for example in amounts of from 0.001 to 0.5% by weight, in the form of aldehydes such as acrolein, glyoxal, propionaldehyde and acetaldehyde; ketones, such as acetone and butanone-2; glycol and higher alkanols such as isobutanol, isopropanol, n-propanol, isohexanol and isoheptanol; hexane; ethers such as dimethyl ether; further organic compounds, for example esters such as dimethyl terephthalate; sulfur compounds, such as dimethyl sulfide; amines, such as monomethylamine, dimethylamine and trimethylamine; amides, such as monemethylformamide and dimethylformamide; and trimethylammonium formate. Which of the above impurities is present in the formaldehyde solution, and in what amount, as a rule depends on the process used. The pH of the solution to be stabilized is suitably from 2 to 6 and preferably from 3 to 4.

The stabilizer can be added as a solid to the solution to be stabilized. However, a more suitable method is first to dissolve the stabilizer, preferably the isophthalo-bis-guanamine, partially or, preferably, completely in a formaldehyde solution of high concentration (stock solution). Compared to the solution to be stabilized, this stock solution preferably has a higher formaldehyde concentration, and the same formic acid concentration and methanol concentration, for example the amounts mentioned above. The amount of stabilizer added is suitably from 0.1 to 1% by weight and preferably from 0.4 to 0.8% by weight, based on stock solution. The stabilizer is added at temperatures of from 40° to 70° C, and especially from 40° to 60° C, with thorough mixing. The rate of solution of the stabilizer increases with increasing formaldehyde concentration, decreasing acid concentration, appropriately increasing pH value and increasing temperature. Advantageously, the stock solution contains from 0.003 to 0.03% by weight of formic acid, or has as pH of from 5.8 to 2.5. If appropriate, the pH of the stock solution is raised before adding the stabilizer, for example by deacidification by means of ion exchangers, neutralization by means of bases, for example sodium hydroxide solution, or production of solutions of low formic acid content by adding secondary amines. For example, the stock solution can be a formaldehyde solution with added amine, such as is obtained in the process, described in German Published Applications Nos. 2,116,947 and 2,201,241, for the manufacture of formaldehyde by oxidative dehydrogenation of methanol with air in the presence of a silver catalyst and using tertiary or secondary amines.

Whilst the stock solution which contains the stabilizer can be stored, for example for from 2 to 8 weeks at from 15° to 30° C, it will as a rule be freshly prepared by the method referred to above and then added to the formaldehyde solution to be stabilized, with thorough mixing. The formaldehyde solution to be stabilized is preferably kept at temperatures from 40° to 80° C, preferably from 50° to 60° C, for 10 to 30 hours before adding the stock solution. The stabilized formaldehyde solution is then stored, preferably at temperatures of from 0° to 60° C and especially from 20° to 45° C. The production of the stock solution and stabilization of the formaldehyde solution with the stabilizer can be carried out at atmospheric or superatmospheric pressure, continuously or batchwise.

The stabilized aqueous formaldehyde solution obtainable by the process of the invention can be used as a disinfectant, tanning agent or reducing agent, and is a valuable starting material for the manufacture of synthetic resins, adhesives and plastics. For uses of the solution, reference may be made to Ullmann, loc.cit., page 670.

The parts referred to in the Examples which follow are by weight.

EXAMPLE 1 a. Preparation of the stock solution: 2.5 parts of isophthalo-bis-guanamine are added to 500 parts of an aqueous solution of 53.25% by weight of formaldehyde, 1.2% by weight of methanol and 0.012% by weight of formic acid (pH 3.1) and the mixture is stirred for 16 hours at 55° C. A clear stock solution is obtained.

b. Stabilization: appropriate amounts of stock solution (a) are added to a 53 per cent and a 52 per cent strength by weight aqueous formaldehyde solution to give the isophthalo-bis-guanamine concentrations (based on the solution) shown in Table I which follows. The solutions to be stabilized each contain 0.012% by weight of formic acid and 1.2% by weight of methanol, have a pH of 3.1 and are kept at 60° C for 16 hours before adding the stock solution. After adding the latter, they are stored at the temperatures shown in Table I. The stabilized solutions do not foam. The pH and formaldehyde concentration do not change on storage.

c. Testing the stability of a formaldehyde solution: in the Examples which follow, a sample of the solution to be tested is kept in a glass flask at a certain temperature in a thermostatic bath. After a certain time, the solution becomes turbid due to precipitation of formaldehyde polymers. The turbidity is followed by a turbidity-meter. The reference standard used in the turbidity meter is an aqueous barium sulfate solution, containing 0.012% by weight of barium sulfate, which is slightly turbid. The point in time at which the turbidity of the solution to be tested is equal to that of the reference solution is taken to be the starting point of instability of the solution. The stability S is defined as the time, in days, until the solution starts to be unstable.

By way of comparison, formaldehyde solutions stabilized as follows are also stored: 2 g of hydroxypropylmethylcellulose are mixed with 30 ml of anhydrous pyridine and 1 g of trimethylchlorosilane is added dropwise, whilst stirring. The reaction is complete after stirring for approx. 5 minutes. The jelly-like solution is then freed from excess pyridine. A 2 per cent strength by weight aqueous solution is prepared from the white residue which remains. A freshly prepared 52 per cent strength by weight formaldehyde solution is divided into 100 g samples. Various amounts of this solution, corresponding to the desired stabilizer concentration, are added to the sample. The samples are stored at 45° C. The solutions foam heavily.

Table I

| Formaldehyde concentration % by weight | Stabilizer concentration % by weight of isophthalo-bis-guanamine | Comparison | Storage temperature ° C | Stability in days S Isophthalo-bis-guanamine | Comparison |
| --- | --- | --- | --- | --- | --- |
| 53 | 0.0010 | — | 50 | 1 | — |
| 53 | 0.0050 | — | 50 | 6 | — |
| 53 | 0.0100 | — | 50 | 35 | — |
| 53 | 0.0150 | — | 50 | 46 | — |
| 53 | 0.0200 | — | 50 | 60 | — |
| 53 | 0.0100 | — | 40 | 0.2 | — |
| 53 | 0.0150 | — | 40 | 1 | — |
| 53 | 0.0200 | — | 40 | 20 | — |
| 52 | 0.0050 | 0.0050 | 45 | 13 | 3 |
| 52 | 0.0100 | 0.0100 | 45 | 38 | 5 |
| 52 | 0.0250 | — | 45 | 60 | — |
| 52 | 0.0500 | 0.0500 | 45 | 60 | 28 |

EXAMPLE 2

The stock solutions, and the solutions to be stabilized, are prepared as described in Example 1. Table II shows the solutions containing the stabilizers according to the invention and those containing o-phthalo-bis-guanamine for comparison, and the results obtained.

Table II

| Formaldehyde Concentration % by weight | Stabilizer % by weight | pH when preparing the solution | Storage temperature, °C | Stability in days | | |
|---|---|---|---|---|---|---|
| | | | | Orthophthalo-bis-guanamine | Isophthalo-bis-guanamine | Terephthalo-bis-guanamine |
| 40 | 0.1000 | 3.4 | −10 | 0.007 | 8 | — |
| 40 | 2.0000 | 3.4 | −10 | 0.5–1 | — | — |
| 36 | 2.000 | 3.4 | −10 | 12 | — | — |
| 40 | 0.0060 | 3.0 | +7 | 0.04 | 4 | — |
| 40 | 0.0080 | 3.0 | +7 | 0.04 | 7 | — |
| 40 | 0.0100 | 3.0 | +7 | 0.04 | 15 | 4 |
| 40 | 0.0150 | 3.0 | +7 | 0.04 | 42 | — |
| 40 | 0.0200 | 3.0 | +7 | 0.04 | 70 | 20 |
| 40 | 0.0300 | 3.0 | +7 | 0.04 | 150 | 26 |
| 50 | 0.0400 | 3.1 | +25 | 0 | 4 | — |
| 50 | 0.0600 | 3.0 | +25 | 0 | 30 | — |
| 50 | 0.1000 | 3.0 | +25 | 0 | 41 | — |
| 50 | 0.5000 | 3.0 | +25 | 0 | 59 | — |

0 = no stabilizing action
— = no test carried out

EXAMPLE 3

Benzoguanamine and caprinoguanamine are used for comparison. The solutions are prepared as in Example 1. The stabilized formaldehyde solutions contain 40% by weight of formaldehyde, 1.6 % by weight of methanol and 0.008% by weight of formic acid. The test is carried out at a temperature of +7° C. The stabilities (in days) are shown in Table III which follows.

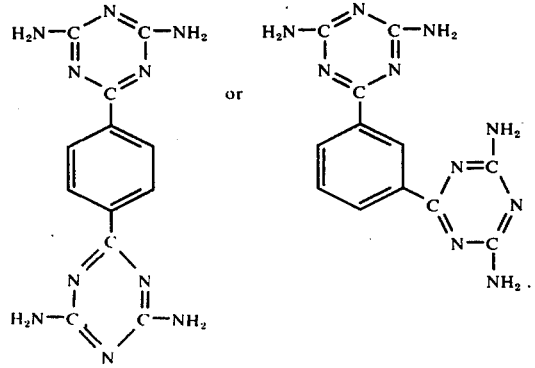

Table III

| | Stabilizer | Stabilizer concentration in % by weight | | | | | | |
|---|---|---|---|---|---|---|---|---|
| | | 0.01 | 0.02 | 0.03 | 0.05 | 0.1 | 0.2 | 0.3 |
| Stability in days | Isophthalo-bis-guanamine | 15 | 70 | 150 | — | — | — | — |
| | Benzoguanamine | 0 | 0 | 0 | 0.1 | 18 | 40 | — |
| | Caprinoguanamine | 0 | 0 | 1 | 2 | 30 | 60 | — |
| | Melamine | 0 | 0 | 0 | 0 | 1 | 2 | 3 |

We claim:
1. An aqueous formaldehyde solution containing a stabilizing amount in the range of 0.001 to 0.5% w/w of the bis-guanamine having the formula

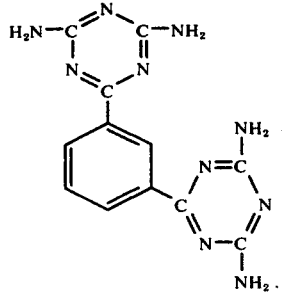

2. An aqueous formaldehyde solution containing a stabilizing amount of a bis-guanamine of the formula 3. An aqueous formaldehyde solution as claimed in claim 2 wherein the amount of said bis-guanamine is in the range of 0.001 to 0.5% by weight, based on the formaldehyde solution.

4. An aqueous formaldehyde solution as claimed in claim 2 wherein the amount of said bis-guanamine is in the range of 0.005 to 0.25% by weight, based on the formaldehyde solution.

5. An aqueous formaldehyde solution as claimed in claim 2 wherein the concentration of the formaldehyde in the aqueous solution is 28 to 65% by weight of formaldehyde.

6. An aqueous formaldehyde solution as claimed in claim 2 wherein the pH of the formaldehyde solution is in the range of 2 to 6.

* * * * *